United States Patent

Tanaka et al.

[11] Patent Number: 5,171,472
[45] Date of Patent: Dec. 15, 1992

[54] PHENYLCYCLOHEXYLDIOXANE DERIVATIVES HAVING AN ETHER BOND FOR ELECTRO-OPTICAL DISPLAYS

[75] Inventors: Yasuyuki Tanaka; Haruyoshi Takatsu; Kiyofumi Takeuchi, all of Tokyo, Japan; Martin Schadt, Seltisberg; Richard Buchecker, Zürich, both of Switzerland

[73] Assignees: Dainippon Ink and Chemicals, Inc., Tokyo, Japan; Hoffman-La Roche Inc., Nutley, N.J.

[21] Appl. No.: 683,009

[22] Filed: Apr. 10, 1991

[30] Foreign Application Priority Data

Apr. 12, 1990 [JP] Japan .................................. 2-97059
Apr. 12, 1990 [JP] Japan .................................. 2-97060
Sep. 26, 1990 [JP] Japan ................................. 2-256518

[51] Int. Cl.$^5$ ............... C09K 19/34; C09K 19/30; C07D 319/06

[52] U.S. Cl. .................... 252/299.61; 252/299.63; 549/374

[58] Field of Search ............... 252/299.01, 299.61, 252/299.63; 359/103, 104; 549/374

[56] References Cited

U.S. PATENT DOCUMENTS 4,784,471 11/1988 Wachtler et al. .................... 359/103

FOREIGN PATENT DOCUMENTS 315014  5/1989 European Pat. Off. .
3705071 9/1988 Fed. Rep. of Germany .
63-44132 2/1988 Japan .
WO86/04895 8/1986 World Int. Prop. O. .
WO91/16321 10/1991 World Int. Prop. O. .

OTHER PUBLICATIONS

Schadt et al, *Applied Physics Letters*, 18 127–128 (1971).
Heilmeier et al, *Proceedings of the I.E.E.E.*, 56, 1162–1171 (1968).
Heilmeier et al, *Applied Physics Letters*, 13 91 (1968).
White et al, *J. App. Physics*, 45, 4718 (1974).
G. Baur, *Mol. Cryst. Liq. Cryst.*, 63, 45 (1981).

*Primary Examiner*—Robert L. Stoll
*Assistant Examiner*—Shean C. Wu
*Attorney, Agent, or Firm*—Armstrong & Kubovcik

[57]  ABSTRACT

A compound represented by formula (I).

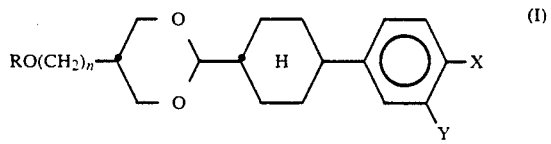

wherein R represents a straight chain alkyl group having 1 to 7 carbon atoms; n is an integer of 1 to 5; X represents F, Cl or CN; Y represents H or F; and a dioxane ring in a trans configuration with respect to a cyyclohexane ring.

4 Claims, No Drawings

PHENYLCYCLOHEXYLDIOXANE DERIVATIVES HAVING AN ETHER BOND FOR ELECTRO-OPTICAL DISPLAYS

BACKGROUND OF THE INVENTION

1. Field of the Invention

This invention relates to phenylcyclohexyldioxane derivatives having an ether bond which are useful as an electro-optical display material.

2. Prior Art

Representative examples of liquid crystal display devices include field-effect mode proposed by M. Schadt, et al., (APPLIED PHYSICS LETTERS, 18, 127–128 (1971)); dynamic scattering mode proposed by G. H. Heilmeier, et al., (PROCEEDING OF THE I.E.E.E., 56, 1162–1171 (1968)); and guest host mode proposed by G. H. Heilmeier, et al., (APPLIED PHYSICS LETTERS, 13, 91 (1968)), or by D. L. White, et al , (JOURNAL OF APPLIED PHYSICS, 45. 4718 (1974)).

Among these types of liquid crystal display devices (LCDs), the twisted nematic liquid crystal display devices (TN-LCDs) which fall in the group of the field-effect mode cells currently are of greatest interest.

As reported by G. Bauer (Mol. Cryst. Liq. Cryst. 63, 45 (1981)), in the TN-LCDs, the product of the anisotropy, $\Delta n$, of refractive index of a liquid crystal material to be filled in a cell, and the thickness d (in $\mu m$) of the liquid crystal layer in the cell must be set to a specified value in order to prevent the occurrence of interference fringes on the surface of the cell, which could impair the appearance of the cell. In cells in practical use, the value of $\Delta n.d$ is set to one of 0.5, 1.0, 1.6 or 2.2. Usually, such cells have a feature that when the value of $\Delta n.d$ is set to 0.5, the visual appearance of the cell is improved, whereas when the value is set to 1.0, 1.6 or 2.2, the contrast of the cell viewed from the front is improved. Therefore, it is usual practice that in the case of liquid crystal display cells in which primary importance is placed on the visual characteristic that the cell be easily visible from all viewing angles, the value of $\Delta n.d$ is set to 0.5; whereas in the case of liquid crystal display cells in which primary importance is attached to the contrast of cells viewed from the front, the value of $\Delta n.d$ is set to 1.0, 1.6, or 2.2.

On the other hand, the thickness d of the liquid crystal layer in liquid crystal display cells in practical use is usually set to a value within the range of 6 to 10 $\mu m$, and hence when the value of $\Delta n.d$ is set to 0.5, liquid crystal material having a small value of $\Delta n$ is required; whereas when the value of $\Delta n.d$ is set to 1.0, 1.6, or 2.2, a liquid crystal material having a large value of $\Delta n$ must be used. As stated above, a liquid crystal material having a small or large value of $\Delta n$ becomes necessary depending on which display characteristics are desired in the liquid crystal display cells.

SUMMARY OF THE INVENTION

It is an object of the present invention to provide a novel nematic liquid crystal compound which when mixed with a liquid crystal matrix can provide a liquid crystal mixture which has a decreased threshold voltage $V_{th}$, a smaller anisotropy in diffractive index $\Delta n$, and a larger anisotropy in dielectric constant $\Delta \epsilon$.

In order to achieve the above-described object, this invention provides a compound represented by general formula (I) below.

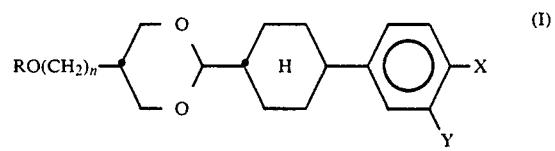

wherein R represents a straight-chain alkyl group having 1 to 7 carbon atoms; n is an integer of 1 to 5; X represents Fluorine (F), Chorine (Cl) or Cyano group (CN); Y represents Hydrogen (H) or F; and a dioxane ring in a trans configuration with respect to a cyclohexane ring.

The compound represented by general formula (I) according to the present invention has a small value of $\Delta n$ and a large value of $\Delta \epsilon$, and as a result, when it is mixed with a nematic liquid crystal mixture which is currently being used generally as the typical liquid crystal matrix, the resulting mixture of a nematic liquid crystal and the conventional liquid crystal matrix can have an increased $\Delta \epsilon$ and a remarkably decreased threshold voltage without decrease or change of $\Delta n$.

Furthermore, the compound of this invention exhibits superior effects to the known compound having a similar chemical structure and is useful as a material for producing TN mode liquid crystal display cells which have excellent visual characteristics and can be driven at low voltages.

DETAILED DESCRIPTION OF THE INVENTION

The compound represented by general formula (I) can be prepared according to the following reaction scheme.

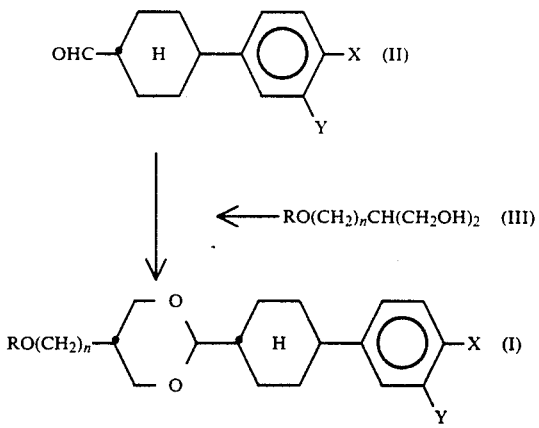

wherein R represents a straight-chain alkyl group having 1 to 7 carbon atoms; n is an integer of 1 to 5; X represents F, Cl or CN; Y represents H or F; and a dioxane ring in a trans configuration with respect to a cyclohexane ring.

The above reaction scheme is to produce a compound represented by general formula (II) and a compound represented by general formula (III) reacted in toluene in the presence of an acidic catalyst such as p-toluenesulfonic acid at a reflux temperature to effect dehydration.

The compound represented by general formula (I) is a nematic liquid crystal compound having a positive anisotropy in dielectric constant, and therefore it can be used, for example, as a material for dynamic scattering mode cells in a state of a mixture with another nematic liquid crystal compound having negative anisotropy in dielectric constant, or as a material for field effect mode cells in a state of mixture with another nematic liquid crystal compound having positive or negative anisotropy in dielectric constant.

Preferred examples of another nematic liquid crystal compound which can be used as an admixture with the liquid crystal compound of the present invention represented by general formula (I) include 4 -substituted benzoic acid-4'-substituted phenyl ester, 4-substituted cyclohexanecarboxylic acid-4'-substituted phenyl ester, 4-substituted cyclohexanecarboxylic acid-4'-substituted biphenyl ester, 4-(4-substituted cyclohexanecarbonyloxy)benzoic acid-4'-substituted phenyl ester, 4-(4-substituted cyclohexyl)benzoic acid-4'-substituted cyclohexyl ester, 4-substituted-4'-substituted biphenyl, 4-substituted phenyl-4'-substituted cyclohexane, 4-substituted-4''-substituted terphenyl, 4-substituted biphenyl-4'-substituted cyclohexane, and 2-(4'-substituted phenyl)-5-substituted pyrimidine.

EXAMPLES

This invention will be described in greater detail by way of examples. However, this invention is not restricted thereto.

In the examples, symbols $T_{C/S}$, $T_{C/N}$, $T_{S/N}$ and $T_{N/I}$ designate a temperature of transition from a crystal phase to a smectic phase, a temperature of transition from a crystal phase to a nematic phase, a temperature of transition form smectic phase to a nematic phase, and a temperature of transition from nematic phase to an isotropic liquid phase, respectively.

EXAMPLE 1

To 3.1 g (0.021 mol) of a compound of formula $CH_3O(CH_2)_3CH(CH_2OH)_2$, and 4.7 g (0.021 mol) of a compound represented by the formula:

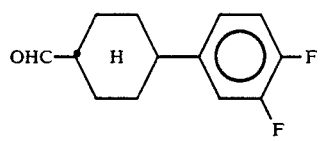

were added 50 ml of toluene and 0.040 g (0.00021 mol) of p-toluenesulfonic acid monohydrate, and the resulting mixture was stirred at a reflux temperature for 3 hours to carry out a dehydration reaction. After cooling the reaction mixture to room temperature, the toluene portion was washed with a saturated aqueous sodium hydrogen carbonate solution and then with saturated saline, and dried. Thereafter, toluene was evaporated off to obtain a crude product.

This product was purified using silica gel column chromatography and then recrystallized from ethanol to obtain 3.8 g (0.011 mol) of a compound represented by the following formula to give a yield of 52%.

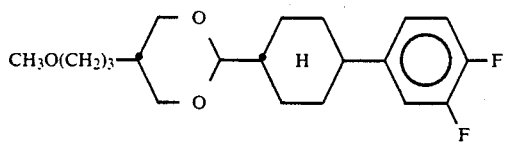

The liquid crystal compound had following transition temperatures; $T_{C/S}$ was 71° C., $T_{S/N}$ was 77° C. and $T_{N/I}$ was 95° C.

EXAMPLE 2

The procedures in Example 1 were repeated except that in place of the compound represented by formula

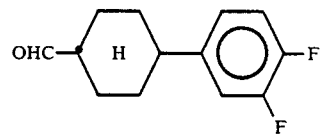

a compound represented by formula

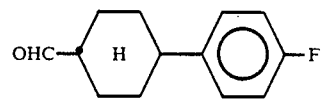

was used to obtain a compound represented by the following formula to give a yield of 62%.

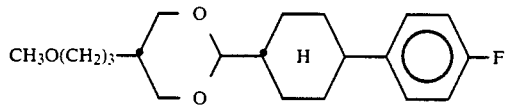

The liquid crystal compound thus obtained had following transition temperatures; $T_{C/N}$ was 107° C. and $T_{N/I}$ was 123° C.

EXAMPLE 3

The procedures in Example 1 were repeated except that in place of the compound represented by formula $CH_3O(CH_2)_3CH(CH_2OH)_2$, a compound represented by formula $CH_3OCH_2CH(CH_2OH)_2$ was used to obtain a compound represented by the following formula to give a yield of 30%.

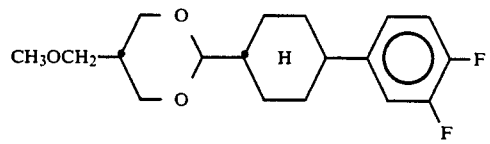

The liquid crystal compound thus obtained had following transition temperatures; $T_{C/N}$ was 81° C. and $T_{N/I}$ was 87° C.

EXAMPLE 4

The procedures in Example 3 were repeated except that in place of the compound represented by formula a compound represented by formula

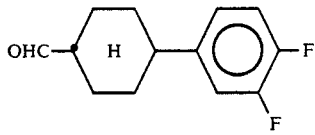

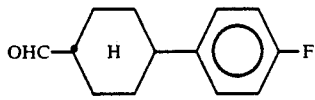

was used to obtain a compound represented by the following formula to give a yield of 23%.

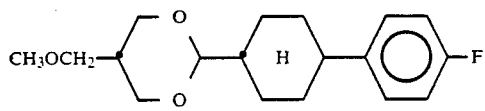

The liquid crystal compound thus obtained had following transition temperatures; $T_{C/N}$ was 95° C. and $T_{N/I}$ was 121° C.

EXAMPLE 5

The procedures in Example 1 were repeated except that in place of the compound represented by formula

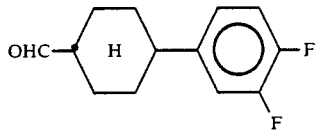

a compound represented by formula

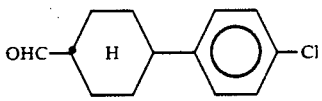

was used to obtain a compound represented by the following formula to give a yield of 61%.

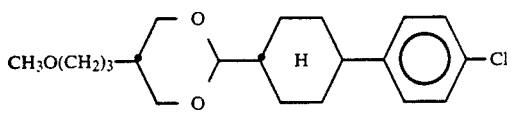

The liquid crystal compound thus obtained had following transition temperatures; $T_{C/S}$ was 80° C., $T_{S/N}$ was 83° C. and $T_{N/I}$ was 142° C.

EXAMPLE 6

The procedures in Example 3 were repeated except that in place of the compound represented by formula a compound represented by formula

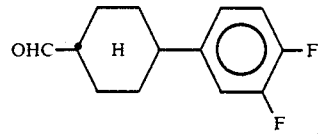

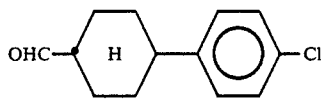

was used to obtain a compound represented by the following formula to give a yield of 17%.

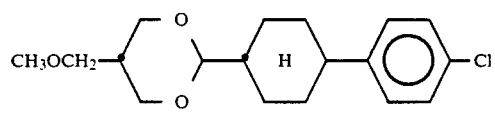

The liquid crystal compound thus obtained had following transition temperatures; $T_{C/N}$ was 89° C. and $T_{N/I}$ was 138° C.

EXAMPLE 7

The procedures in Example 1 were repeated except that in place of the compound represented by formula

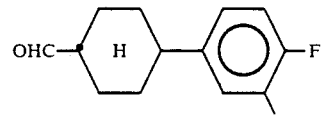

a compound represented by formula

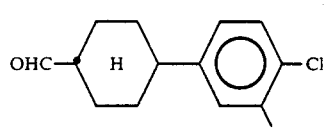

was used to obtain a compound represented by the following formula to give a Yield of 56%.

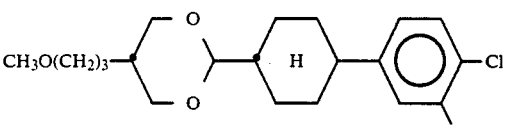

The liquid crystal compound thus obtained had following transition temperatures; $T_{C/N}$ was 82° C. and $T_{N/I}$ was 106° C.

EXAMPLE 8

The procedures in Example 3 were repeated except that in place of the compound represented by formula

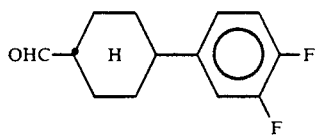

5.0 g (0.023 mol) of a compound represented by formula

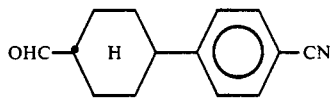

was used to obtain a compound represented by the following formula to give a yield of 36%.

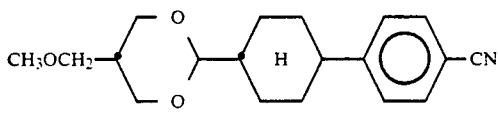

The liquid crystal compound thus obtained had following transition temperatures; $T_{C/N}$ was 115° C. and $T_{N/I}$ was 209° C.

EXAMPLE 9

The procedures in Example 1 were repeated except that in place of the compound represented by formula

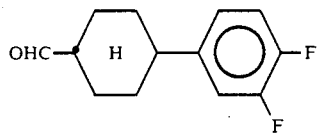

a compound represented by formula

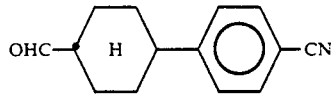

was used to obtain a compound represented by the following formula to give a yield of 53%.

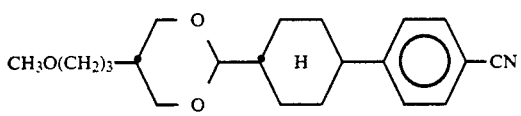

The liquid crystal compound thus obtained had following transition temperatures; $T_{C/N}$ was 117° C. and $T_{N/I}$ was 200° C.

EXAMPLE 10

The procedures in Example 1 were repeated except that in place of the compound represented by formula

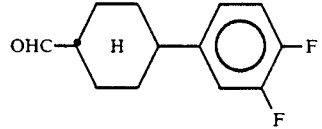

a compound represented by formula

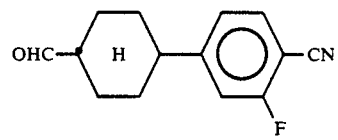

was used to obtain a compound represented by the following formula to give a yield of 49%.

CH₃O(CH₂)₃—[formula]—CN, F

The liquid crystal compound thus obtained had following transition temperatures; $T_{C/N}$ was 103° C. and $T_{N/I}$ was 162° C.

Table 1 below shows the phase transition temperatures of the liquid crystal compounds obtained in Examples 1 to 10, respectively.

TABLE 1

CH₃O(CH₂)ₙ—[structure]—X, Y

| Example | n in Formula (I) | X | Y | Phase Transition Temperature (°C.) | | |
|---|---|---|---|---|---|---|
| 1 | 3 | F | F | $T_{C/S}$:71 | $T_{S/N}$:77 | $T_{N/I}$:95 |
| 2 | 3 | F | H | $T_{C/N}$:107 | $T_{N/I}$:123 | |
| 3 | 1 | F | F | $T_{C/N}$:81 | $T_{N/I}$:87 | |
| 4 | 1 | F | H | $T_{C/N}$:95 | $T_{N/I}$:121 | |
| 5 | 3 | Cl | H | $T_{C/S}$:80 | $T_{S/N}$:83 | $T_{N/I}$:142 |
| 6 | 1 | Cl | H | $T_{C/N}$:89 | $T_{N/I}$:138 | |
| 7 | 3 | Cl | F | $T_{C/N}$:82 | $T_{N/I}$:106 | |
| 8 | 1 | CN | H | $T_{C/N}$:115 | $T_{N/I}$:209 | |
| 9 | 3 | CN | H | $T_{C/N}$:117 | $T_{N/I}$:200 | |
| 10 | 3 | CN | F | $T_{C/N}$:103 | $T_{N/I}$:162 | |

In Table 1, symbols $T_{C/S}$, $T_{C/N}$, $T_{S/N}$ and $T_{N/I}$ designate a transition temperature from a crystal phase to a smectic phase, a transition temperature from a crystal phase to a nematic phase, a transition temperature from a smectic phase to a nematic phase and a transition temperature from a nematic phase to an isotropic liquid phase, respectively.

APPLICATION EXAMPLE

Ten liquid crystal mixtures composed of 80% by weight of the liquid crystal matrix (A), described below currently in general use as a nematic liquid crystal material and 20% by weight of the liquid crystals obtained in Examples 1 to 10, was examined to measure its threshold voltage, anisotropy in refractive index Δn, and anisotropy in dielectric constant Δε. For comparison, the threshold voltage of the liquid crystal matrix (A) itself was measured, as well a liquid crystal mixture composed of 80% by weight of the liquid crystal matrix (A) and 20% by weight of a liquid crystal compound (a) having a chemical structure similar to that of the liquid crystal compound obtained in Example 1. Table 2 shows the results obtained.

TABLE 2

| Liquid Crystal | Δn | Δε | Threshold Voltage (V) |
|---|---|---|---|
| (A) alone | 0.092 | 6.7 | 1.60 |
| (A) and Compound of Example 1 | 0.090 | 8.1 | 1.35 |
| (A) and Compound of Example 2 | 0.092 | 7.3 | 1.52 |
| (A) and Compound of Example 3 | 0.089 | 8.9 | 1.29 |
| (A) and Compound of Example 4 | 0.092 | 7.8 | 1.46 |
| (A) and Compound of Example 5 | 0.098 | 8.5 | 1.56 |
| (A) and Compound of Example 6 | 0.098 | 8.9 | 1.47 |
| (A) and Compound of Example 7 | 0.096 | 9.3 | 1.39 |
| (A) and Compound of Example 8 | 0.106 | 12.6 | 1.40 |
| (A) and Compound of Example 9 | 0.105 | 10.0 | 1.47 |
| (A) and Compound of Example 10 | 0.100 | 11.7 | 1.29 |
| (A) and compound (a) | 0.096 | 6.2 | 1.92 |

The liquid crystal matrix (A) has the following composition:

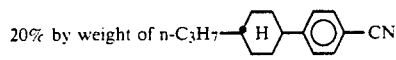

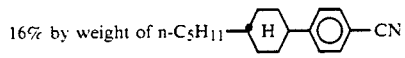

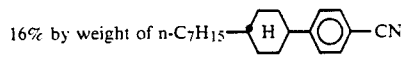

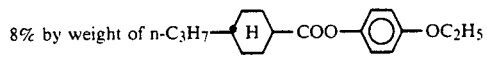

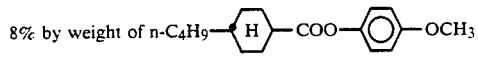

-continued

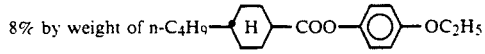

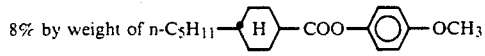

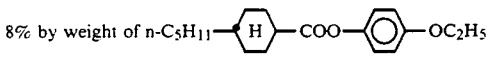

The liquid crystal compound (a) is a known compound (cf. Japanese Patent Publication No. 44132/1988) represented by the following formula

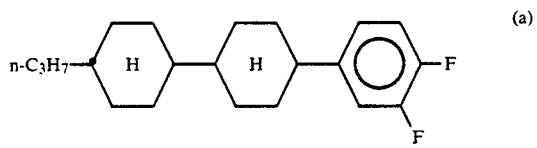

The results shown in Table 2 confirmed that the mixing of the known liquid crystal compound (a) with the liquid crystal matrix (A) gave rise to undesirably increased Δn, decreased Δε, and considerably elevated threshold voltage, to the mother liquid crystal (A), in contrast to the liquid crystal compound represented by formula (I) according to the present invention gave rise to an increased Δε and remarkably decreased threshold voltage without decrease or change of Δn, of the liquid crystal mixture.

What is claimed is:

1. A compound represented by formula (I)

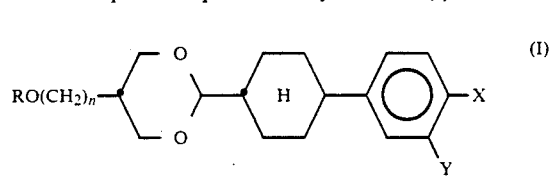

wherein R represents a straight chain alkyl group having 1 to 7 carbon atoms; n is an integer of 1 to 5; X represents Fluorine (F), Chlorine (Cl) or cyano group (CN); Y represents Hydrogen (H) or Fluorine (F); and a dioxane ring in a trans configuration with respect to a cyclohexane ring.

2. The compound as claimed in claim 1, wherein X represents F or Cl.

3. The compound as claimed in claim 1, wherein X is CN.

4. A liquid crystal mixture consisting essentially of the compound as claimed in claim 1.